United States Patent
Keshelava et al.

(10) Patent No.: US 11,260,347 B2
(45) Date of Patent: Mar. 1, 2022

(54) METHOD AND DEVICE FOR SEPARATING EXTRACELLULAR VESICLES FROM BIOLOGICAL LIQUIDS WITH THE AID OF CASCADE ULTRAFILTRATION

(71) Applicant: LIMITED LIABILITY COMPANY "PROSTAGNOST", Moscow (RU)

(72) Inventors: Varlam Borisovich Keshelava, Moscow (RU); Marina Yurievna Zemskova, Pushchino (RU); Konstantin Sergeevich Sorokin, Korolev (RU)

(73) Assignee: LIMITED LIABILITY COMPANY "PROSTAGNOST", Moscow (RU)

( * ) Notice: Subject to any disclaimer, the term of this patent is extended or adjusted under 35 U.S.C. 154(b) by 65 days.

(21) Appl. No.: 16/955,186

(22) PCT Filed: Dec. 26, 2017

(86) PCT No.: PCT/RU2017/000976
§ 371 (c)(1),
(2) Date: Jun. 18, 2020

(87) PCT Pub. No.: WO2019/132688
PCT Pub. Date: Jul. 4, 2019

(65) Prior Publication Data
US 2020/0330922 A1    Oct. 22, 2020

Related U.S. Application Data

(63) Continuation of application No. PCT/RU2017/000976, filed on Dec. 26, 2017.

(51) Int. Cl.
*B01D 61/18* (2006.01)
*B01D 61/58* (2006.01)
*C12N 15/10* (2006.01)

(52) U.S. Cl.
CPC ............ *B01D 61/18* (2013.01); *B01D 61/58* (2013.01); *C12N 15/1017* (2013.01)

(58) Field of Classification Search
CPC .. B01D 61/18; B01D 61/58; B01D 2319/025; B01D 2325/02; B01D 69/02;
(Continued)

(56) References Cited

U.S. PATENT DOCUMENTS

| 2015/0353920 A1* | 12/2015 | Enderle ............. C12N 15/1006 536/25.41 |
| 2017/0173537 A1* | 6/2017 | Gagnon ................... C07K 1/34 |
| 2019/0201341 A1* | 7/2019 | Morton ................ A61K 9/1277 |

OTHER PUBLICATIONS

Heinemann et al "Sequential filtration: a gentle method for the isolation of functinoal extracellular vesicles", Springer Science + business mediq LLC, Aug. 22, 2017.*

* cited by examiner

*Primary Examiner* — Krishnan S Menon
(74) *Attorney, Agent, or Firm* — Nixon & Vanderhye PC

(57) ABSTRACT

This invention describes a method and a device for efficient isolation of extracellular vesicles from animal and human biological fluids, as well as from culture fluid using equipment of standard diagnostic laboratories, that is, without the use of ultracentrifugation. These method and device can be applied for the diagnosis of various human diseases, as well as for therapeutic purposes, if the purified vesicles are used as an agent for drug delivery to the cells of the body. The device for the purification of extracellular vesicles contains at least two membrane filters: the first filter containing a membrane with pore sizes in the range from 400 to 600 nm, connected to the second filter containing a membrane with pores in the range from 95 to 200 nm. At the same time, the membranes of these filters are made of materials that practically do not bind biological polymers.

10 Claims, 12 Drawing Sheets

(58) Field of Classification Search
CPC ........ B01D 71/68; B01D 71/16; B01D 71/10; B01D 61/142; B01D 63/087; B01D 61/14; C12N 15/1017
See application file for complete search history.

METHOD AND DEVICE FOR SEPARATING EXTRACELLULAR VESICLES FROM BIOLOGICAL LIQUIDS WITH THE AID OF CASCADE ULTRAFILTRATION

This application is a continuation of International Application No. PCT/RU2017/000976 filed Dec. 26, 2017, the entire content of which is hereby incorporated by reference.

FIELD OF THE INVENTION

The present invention relates to method and a device for isolation and purification of extracellular vesicles, including exosomes, from biological samples, including animal and human body fluids. The present invention further relates to the use of purified extracellular vesicles for various purposes in diagnostics and therapy.

BACKGROUND

Extracellular vesicles, such as exosomes (with a diameter of 40-150 nanometers (nm)), prostasomes (with a diameter of 40-500 nm), microvesicles (with a diameter of 100-1000 nm) and apoptotic bodies (with a diameter of 800-5,000 nm), are membrane spheroids, secreted into the extracellular space by cells of various tissues and organs both under normal and pathological conditions. These particles can be found in almost any biological fluid, such as a (culture) medium for cell culture growth, blood plasma, urine, synovial fluid, cerebrospinal fluid, saliva, tear, seminal fluid, milk, etc. These vesicles contain certain specific composition of molecules, including proteins, lipids, metabolites, and nucleic acids that are common for maternal cells. Exosomes, microvesicles, and apoptotic bodies differ significantly in terms of biological molecules content such as ribosomal RNA, microRNA and protein markers (Crescitelli R J, et al., *Extracell Vesicles,* 2013 Sep. 12; 2). Vesicles are formed by budding from the cell plasma membrane and therefore their contest is enclosed in a bi-layer membrane containing various microdomains (for example, enriched in cholesterol, sphingolipids, etc.).

Vesicles are of a special interest because their content can be used to diagnose the state of the cells that secreted them. The possibility to isolate them from body fluids and their information content make them ideal non invasive biomarkers of many diseases, for example, cancer (Fais S, et al., *ACS Nano,* 2016, Apr. 26; 10 (4): 3886-99). In addition, they can also be used for targeted delivery of specific drugs. In order to use the diagnostic and therapeutic potential of exosomes entirely, it is required to develop reproducible, specific and easy-to-use methods of purifying exosomes from biological fluids.

There are many methods of vesicles, and exosomes purification described, in particular, (Pin Li, et al., "Progress in Exosome Isolation Techniques", *Theranostics,* 2017, Vol. 7, Issue 3, 789-804). The traditional method of vesicles isolation is based on ultracentrifugation of a biological fluid under such conditions as, for example, at 100,000×g for several hours (Kosanovic M and Jankovic M, *BioTechniques,* 2014, 57: 143-149), however it was noted that the isolated exosome fraction was contaminated by cellular and protein debris. Exosomes can also be isolated based on their floating density in viscous fluids when samples with exosomes are layered on top of a gradient of sucrose or other substance and are subjected to high-speed ultracentrifugation (Alvarez M L et al., *Kidney Int.,* 2012, 82: 1024-1032; Gerlach J, et al., *PLoS ONE,* 2013, Sep. 19; 8 (9): e74801). The advantage of this method is in an increased purity of the exosomal fraction, but at the same time, this method is labor and time-consuming, not suitable for the analysis of a large number of samples, and results in the loss of a significant number of exosomes (Lane R E, et al., *Sci Rep.,* 2015, Jan. 6; 5: 7639).

Another approach for extracellular vesicles isolation is described in patent application US 20170198280 A1; it is specifically designed for the analysis of nucleic acids contained in exosomes, since it uses centrifuge columns with positively charged membranes that provide electrostatic interaction with nucleic acids. Moreover, the vesicles undergo lysis in the process of elution. Several commercially available kits for exosomes purification from heterogeneous biological samples have been developed, such as the Invitrogen Total Exosome Isolation Kit (Life Technologies, USA) and ExoSpin Exosome Purification Kit (Cell Guidance Systems, USA). These two kits stimulate the precipitation of vesicles by adding polyethylene glycol or similar substances, and the complexes of exosomes with polyethylene glycol are precipitated from the solution at a low centrifugation speed (10,000-20,000×g). While this method is less labor consuming and does not use ultracentrifugation, it facilitates the precipitation of not only exosomes, but of cell debris and protein fractions as well (Oosthuyzen W, et al., *J Physiol.,* 2013 Dec. 1; 591 (23): 5833-42) The presence of proteins and other polymers from biological fluids in the exosome fraction significantly complicates subsequent diagnostic procedures and reduces their sensitivity. Finally, other exosome isolation methods are described in US 20160333338 A1, RU 2556825, and US 20150024949 A1.

The methods of exosomes purification and isolation from biological fluids, which are currently available on the market and described in the literature, do not meet the growing demand for easy-to-use and reliable methods that can be applied in standard diagnostic laboratories. Since the importance of the diagnostic and therapeutic potential of exosomes cannot be overestimated, there is a need for new, improved methods for isolating intact exosomes from biological fluids for subsequent analysis or modification for therapeutic applications. The claimed invention has a number of advantages that makes it suitable for the problem solution and for wide application in standard diagnostic practice.

SUMMARY OF THE INVENTION

The objective of this invention is to provide a simple and effective method of purifying extracellular vesicles from animal body fluids, which can be applicable in a standard diagnostic practice, which means, without using expensive tools such as the ultracentrifuge.

The solution of the problem is to use two-stage filtration of a biological fluid through filter, the membrane of which does not bind biological polymers, including those located on the surfaces of the vesicles. In this case, the purification efficiency is determined by the size of the vesicles and does not depend on their cell origin or on the presence of certain epitopes on the surface. The filtration parameters chosen make it possible to free the vesicle fraction both from most major proteins present in body fluids and from microcomplexes larger than 500 nm, including cells, cell fragments, apoptotic bodies, etc.

In some embodiments of the invention, this objective is achieved by a method of isolating extracellular vesicles from a sample of the subject's biological fluid, including at least the following steps: (a) to obtain a sample of biological fluid; (b) to filter the sample of biological fluid at least once through the first membrane filter containing a membrane that practically does not bind biological polymers and has pore sizes in the range from 400-600 nm; (c) to filter the solution obtained from step (b) at least once through the second membrane filter containing a membrane that practically does not bind biological polymers and has pore sizes ranging from 100-200 nm; (d) to rinse the material located on the second filter surface; (e) to harvest the material that has not passed through the second filter from the surface of the second filter, the material mentioned consists primarily of extracellular vesicles. In some embodiments of the invention, the filter membrane, which practically does not bind biological polymers, is made of: cellulose acetate, regenerated cellulose, polyethersulfone or aramid. In the preferred embodiments of the invention, the second membrane filter has pore sizes ranging from 95 to 105 nm.

In some embodiments of the invention, the material that has not passed through the second filter is harvested by the reverse flow of the rinsing buffer.

In some embodiments of the invention, the objective is achieved by a method of extracellular vesicles isolation, which includes passing the material through the first or the second membrane filter at least two times.

In the preferred embodiments of the invention, a method for isolating extracellular vesicles is characterized by using centrifugation or vacuum filtration to increase the speed of passing the biological fluid through the first or the second membrane filter. In some embodiments of the invention, centrifugation or vacuum filtration with the purpose of increasing the filtration speed are used in any combination, namely, vacuum for the first filter and vacuum for the second filter; vacuum for the first filter and a centrifuge for the second filter; a centrifuge for the first filter and vacuum for the second filter; a centrifuge for the first filter; and a centrifuge for the second filter.

In some embodiments of the invention, the method of vesicles isolation is wherein the initial biological fluid from which the vesicles to be isolated is any biological fluid listed below: plasma or blood serum, urine, synovial fluid, cerebrospinal fluid, saliva, tear, seminal fluid, milk and others. Also, this method is applicable for the isolation of vesicles from the culture media used for cell growth in vitro. In the preferred embodiments of the invention, the biological fluid from which extracellular vesicles are isolated is urine.

In some embodiments of the invention, in order to minimize loss of the exosomes fraction, a double side ultrafiltration method is applied to the material passing through the second filter membrane. This involves filtering by any method described, after which the harvested material is rinsed via the reverse flow of the rinsing buffer. This is done in order to extract the smallest exosome fraction more completely as this fraction can penetrate the subsurface layer of the filter.

In the preferred embodiments of the invention, the described methods of extracellular vesicles isolation can be used for the purpose of diagnosing, predicting the development, or determining the risk of developing a disease in the subject. In some embodiments of the invention, medical indications for using this method of vesicles isolation are selected from the diseases of the organs and tissues of the genitourinary system, or cancer diseases, for example, malignant diseases of the hematopoietic system, prostate gland, bladder, kidney, or other organs and tissues.

In some embodiments, filtering can be sequential when the sample is passed through the first filter and then through the second, otherwise the sample can be passed through a double filter at the same time.

In some embodiments, the first, the second, or both stages of filtration are accelerated by vacuum filtration.

In some embodiments, the first, the second, or both stages of filtration are accelerated by centrifugation at 3-6,000 g.

Sequential ultrafiltration can be any combination of vacuum and centrifugal ultrafiltration: vacuum-vacuum, vacuum-centrifuge, centrifuge-vacuum, and centrifuge-centrifuge.

In some embodiments of the invention, the mentioned above objective is achieved with the help of a device for implementing the methods of extracellular vesicles isolation from a sample of biological fluid of the subject. It includes the first membrane filter containing a membrane with pore sizes in the range from 400 to 600 nm, which is connected to the second membrane filter containing a membrane with pore sizes ranging from 95 to 200 nm. The membranes of these filters are made of materials that practically do not bind biological polymers, and the device itself is configured to filter a sample of biological fluid through both of these filters. In some embodiments of the invention, the objective mentioned above is achieved using a device with a special design, corresponding to the implementation of each of the above methods. For example, the implementation of the single-stage double ultrafiltration can be vacuum or centrifugal. The design for vacuum one-stage double ultrafiltration preferably uses a vacuum ultrafiltration system, which is similar in structure to the standard one, but it has a cylindrical funnel, which ensures a tight fit of the inner cylinder inserted into the funnel. The first filter with pore sizes of 400-500 nm is installed on the bottom of the cylinder, while the second filter, 100-200 nm, is located below the first one. In the case of double ultrafiltration by centrifugation, a double insert is preferably used in a centrifuge tube having a "cylinder-in-cylinder" design. The first membrane with a pore size of 400-600 nm is hermetically inserted into the bottom of the inner cylinder, which the processed fluid enters, and the second membrane with a pore size of 95-200 nm is hermetically inserted into the bottom of the outer cylinder.

In some cases, when the initial sample contains a large number of large particles and polymers clogging the first filter, the filtration procedure can be performed after the preliminary centrifugation up to 15,000 g.

In some cases, after the preliminary centrifugation up to 15,000 g. it is possible to obtain material of such purity that it can be directly filtered through the second filter of 95-200 nm.

For ultrafiltration, well-wettable filters with a zero or negligible charge are mainly used (very lightly binding or completely not binding to biological polymers such as DNA, RNA, proteins, lipids, polysaccharides, etc.). Examples of membrane materials for such filters are cellulose acetate, regenerated cellulose, or polyethersulfone. It can also be any other filter with a suitable pore size made of (or at least one filtering side made of) materials that are non-ionizing under the isolation conditions and that do not bind the polymers present in biological samples.

It is possible to use a membrane with a substrate or a filter with a modified top layer with the required properties as the second filter.

By implementing this invention, the following technical result is achieved: a new effective method has been developed for purifying whole, intact, not contaminated extracellular vesicles from 40 to 400 nm in size from a wide range of animal and human biological fluids, such as blood plasma, urine, synovial fluid, cerebrospinal fluid, saliva, tear, seminal fluid, milk and others. The method described allows to effectively purify extracellular vesicles from animal and human biological fluids in a standard diagnostic laboratory, that is, without the use of expensive tools, such as ultracentrifuges. The method described demonstrates a greater speed, simplicity and a higher degree of purification for a comparable amount of isolated vesicles compared to other methods of vesicles purification that do not use ultracentrifugation.

BRIEF DESCRIPTION OF THE DRAWINGS

FIG. 7. Analysis of exosomes on a Zetasizer NanoZS device isolated by salting-out.

FIG. 8. An embodiment of a method for isolating exosomes that harvests and rinses exosomes using vacuum ultrafiltration.

FIG. 9. Analysis of exosomes on a Zetasizer NanoZS device isolated by the filtration method using filters with pore sizes of 0.05 μm. Contamination of the preparation of exosomes by urine proteins adsorbed on the filter is indicated by the arrows.

FIG. 10. Analysis of exosomes on a Zetasizer NanoZS device isolated by the claimed filtration method using filters with pore sizes of 0.1 μm. The arrows indicate the absence of contamination of exosome preparations by urine proteins that were detected in other tests and which are determined within the size range from 1 to 10 nm.

DETAILED DESCRIPTION OF THE INVENTION

Figure 1:
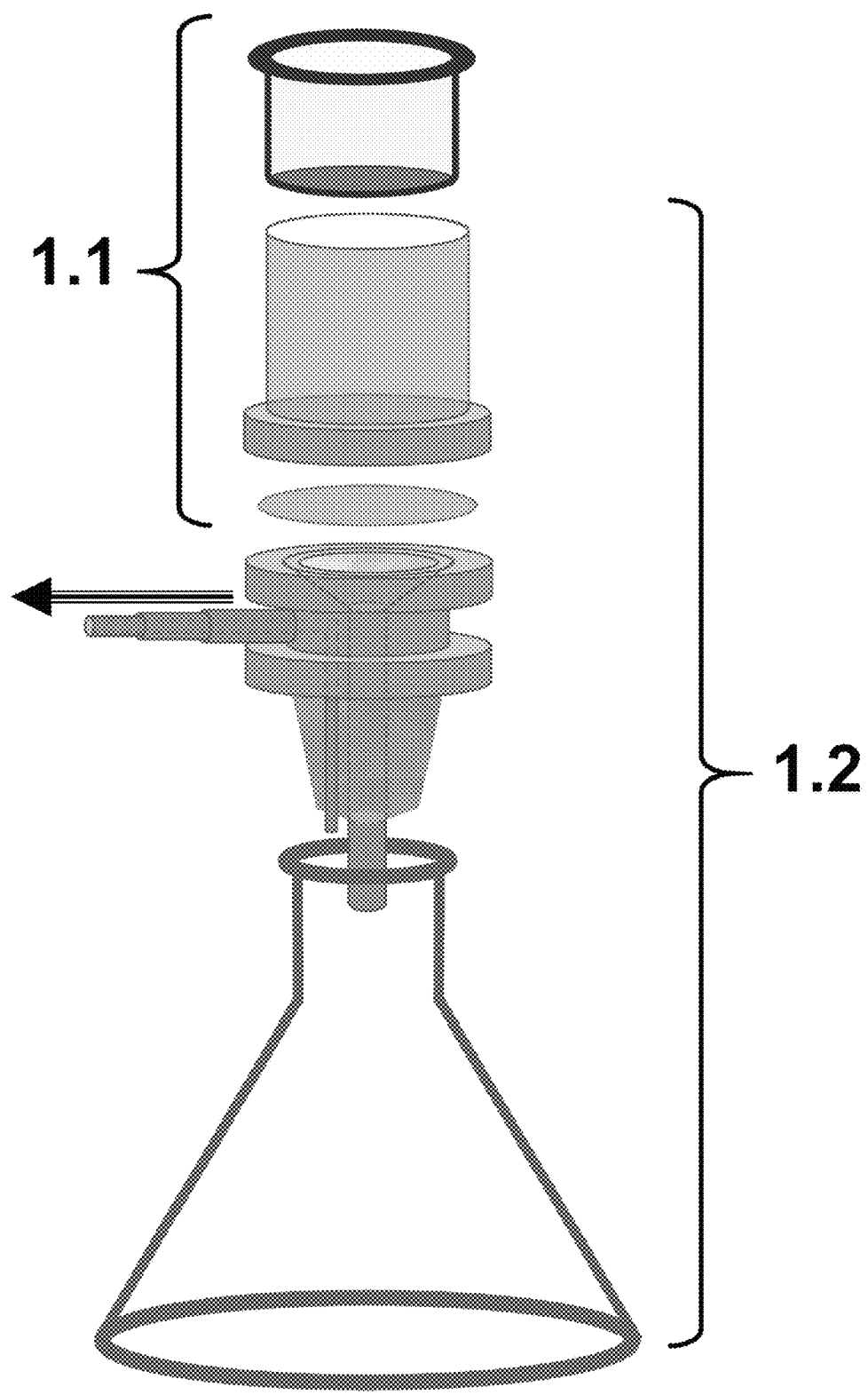
FIG. 1. The ultrafiltration system for double simultaneous filtration by vacuum. 1.1—Double membrane cartridge for vacuum ultrafiltration. 1.2—A version of the device for laboratory ultrafiltration, which features a cylindrical funnel, hermetically enclosing a membrane cartridge.

In the description of this invention, the terms "includes" and "including," are interpreted as "includes, but is not limited to." These terms are not intended to be interpreted as "consists only of".

Unless defined separately, the technical and scientific terms in this application have standard meanings generally accepted in the scientific and technical literature.

Terms "extracellular vesicles" and "vesicles" covers all membrane vesicles released by cells, while the terms "exosomes", "prostasomes", "microvesicles", "apoptotic bodies", and "microsomes" are used for specific populations of extracellular vesicles. Exosomes, the most studied of extracellular vesicles, are small membrane vesicles (40-150 nm) of intracellular origin. The exosomes secreted by the prostate (referred to as "prostasomes"; described, for example, in Ronquist G, et al., *The Prostate*, 2012 Wiley Periodicals, p. 1-10), can reach a diameter of 500 nm. Another common type of extracellular vesicles are microvesicles, which are thought to have a typical diameter of 100-1000 nm and are released by budding of the plasma cell membrane. Apoptotic cells form irregular buds of the plasma membrane; when the cell is destroyed, membrane vesicles called apoptotic bodies are formed with sizes of 800-5000 nm. Microsomes are small vesicles with a diameter of 80-120 nm, formed from fragments of the membrane of the endoplasmic reticulum during ultracentrifugation of homogenized cells.

There are several commonly used terms In English-language scientific and technical literature to name the process we describe. So, in the description of this invention, terms "purification", "isolation" and "extraction" in relation to extracellular vesicles should be treated as a synonyms.

The material of the filter membrane, which practically does not bind biological polymers, has a meaning of a material that is well wetted by water with a zero or negligible charge generated during wetting, which ensures the absence of electrostatic, dipole-dipole, hydrophobic, van der Waals, and other interactions at the contact of the membrane material with biological polymers, such as DNA, RNA, proteins, lipids, polysaccharides, etc. Examples of membrane materials for such filters are cellulose acetate, regenerated cellulose, polyethersulfone, and some others.

Vacuum filtration should be understood as a method of filtering (filtration) fluids, where the difference between the atmospheric pressure outside the filtrate receiver and the artificially reduced pressure (vacuum) inside is used to move the filtered fluid through the filtering element.

The following examples are provided in order to disclose the characteristics of this invention and should not be interpreted as limiting the scope of the invention in any way.

Development of the Method of Purification of Exosomes from Body Fluids

Since the diagnostic and therapeutic potential of exosomes is significant, the procedure for their purification should be simple and reliable, and result in the isolation of a fraction of exosomal particles with a size of 0.04-0.5 micrometers (μm) from biological fluids and has to be free of proteins and other biological polymers. Biological fluids are complex mixtures, containing particles both larger and smaller than the required range; they contain polymers, for example, proteins, of different molecular weights, which can form aggregates when interacting with each other. Such complexes may form flakes or a jelly-like precipitate. Polymer molecules and their aggregates cover the entire spectrum of filtration size. The low molecular weight fraction passes all the stages of filtration, and the largest formations prevent ultrafiltration by clogging the filters or forming a jelly-like layer on the filter surface. The solution to this problem is presented as a filtration system, which should not only retain particles larger in size than 40 nm, but also additionally cut off formations larger than 400 nm, and at the same time additionally ensure the removal of the bulk of soluble proteins.

There are various filters available with a number of different properties affecting their applicability for solving a particular problem. The most important difference between filters is the chemical nature of the material the filter is made of The filter's material defines a number of very important parameters:

1) the wettability (hydrophilicity-hydrophobicity) of the membrane strongly affects the process of the fluid flow. If the pores are small, the filter must necessarily be made of a wettable material, otherwise the surface tension can simply keep the fluid layer on the surface, preventing its penetration into the filter thickness. In the case of biological samples, it is water wettability, which is referred to as hydrophilicity.

2) ionization of the material in water; this may result in charging the filter surface. This charge can lead to the effect of retaining the molecules and/or the particles that have an opposite charge. If the membrane is significantly charged, the binding effect can be almost irreversible. If the charge is lower, the binding is reversible and the molecules and/or particles can be detached again. However, even with small charges of a membrane, it interacts with various biological molecules and particles, which may also be charged.

Currently, there is no accurate data on the nature and the constancy of the charge of exosomes; therefore, in order to purify exosomes, it is required to use a well-wettable filter with a zero or negligible charge (very slightly or completely not binding to biological polymers: DNA, RNA, proteins, lipids, polysaccharides and etc.). Examples of membrane materials for such filters are cellulose acetate, regenerated cellulose, polyethersulfone, and some others. Also, any other filter with a suitable pore size made of (or at least one filter side made of) non-ionizing material that does not bind to polymers present in the biological samples can be used for the invention implementation.

3) Another important characteristic of filters is the average pore size and the pore size distribution. There is another issue here as the filters with small pores are most often used for the separation of polymers and are well characterized by the parameters of interaction with them. The most common characteristic of the filter is the minimum molecular weight of the polymer retained in MWCO (molecular-weight cut-off). However, the starch molecule and the protein molecule will behave differently on the same filter, even if both have the same molecular weight. Manufacturers admit that the MWCO parameter is approximate and there is a correlation between it and the average pore size, but it may significantly vary for filters made of different materials and by different technologies.

Moreover, if we consider the range of particle size of 0.04-0.5 μm and, accordingly, the filters with similar pore sizes, a layer of bound water occurs on the hydrophilic surface. This layer has a minimum thickness of about 5 nm, and it can reach up to 30 nm. Thus, the filter's effective transmission size can be significantly smaller than the average pore size. Based on this, for example, under appropriate conditions it is possible to retain vesicles with a diameter of 0.05 μm on a 0.1 μm filter.

Consequently, for the effective purification of exosomes from biological fluids, it is necessary: (1) to separate particles, flakes and other formations larger than 0.4-0.5 microns and the jelly-like products of the interaction of dissolved polymers (most often proteins) with each other; (2) to separate the maximum number of remaining particles larger than 0.04-0.5 μm from the sample, while it is desirable to keep the intact vesicles on the surface of the filter for their further use; (3) to use lightly charged or uncharged wettable filters that do not bind, or minimally bind, biological macromolecules, which will allow (a) to filter large volumes of samples, due to the fact that such a filter is not covered by polymers bound to it and retains its filtering ability longer, and (b) to get rid of the dissolved macromolecules by rinsing the mass of the isolated particles with a fresh buffer.

Thus, for the implementation of the invention by the specified method, it is necessary to obtain a sample of the original biological fluid from which the vesicles have to be isolated. The sample can be any human body fluid, such as blood plasma, urine, synovial fluid, cerebrospinal fluid, saliva, tear, seminal fluid, milk, prostate juice, and others, as well as the culture media used for cell growth. It is further necessary to pass this sample at least once through the first membrane filter containing a membrane that practically does not bind biological polymers and has pore sizes in the range from 400 to 600 nm. After that, it is necessary to pass the solution, which has already passed through the first filter, at least once through the second membrane filter containing a membrane that practically does not bind biological polymers and has pore sizes in the range from 95 to 200 nm. Next, the material that has not passed through the second filter must be harvested from the surface of the second filter.

This invention uses sequential ultrafiltration of the biological fluid through two or more hydrophilic filters that do not bind to biological polymers. Such a system can be implemented in a universal way as a set of filtering devices in which the sample undergoes sequential processing, and the filters are selected in such a way that 1. the first filter with an average pore diameter of 0.45-0.5 µm ensures the retention of large particles and aggregates/flakes of macromolecules by passing microparticles smaller than 450 nm in size and molecules dissolved in fluids, including polymers;

2. the second filter, with an average pore diameter of 0.1-0.15 µm, provides the retention of microparticles larger than 40 nm, passing smaller molecules dissolved in fluids.

In some embodiments, the pore sizes of the first filter are 0.4 µm, 0.45 µm, 0.5 µm, 0.55 µm, or 0.6 µm. In some embodiments, the pore sizes of the second filter are 0.1 µm, 0.15 µm, or 0.2 µm.

When implementing the claimed method, both vacuum and centrifugation can be used as an inducer of the fluid flow through the filter. The design of the filtration unit can be in the form of a cylinder liner, forming a double membrane cartridge, and the inducer of the flow can be reduced air pressure at the outlet of the filtration system (vacuum ultrafiltration, see FIG. 1).

Alternatively, a pair of cylinder liners may be placed in a centrifuge tube (FIG. 2), and low-speed centrifugation (centrifugal ultrafiltration) can be the inducer of the flow.

Figure 2:
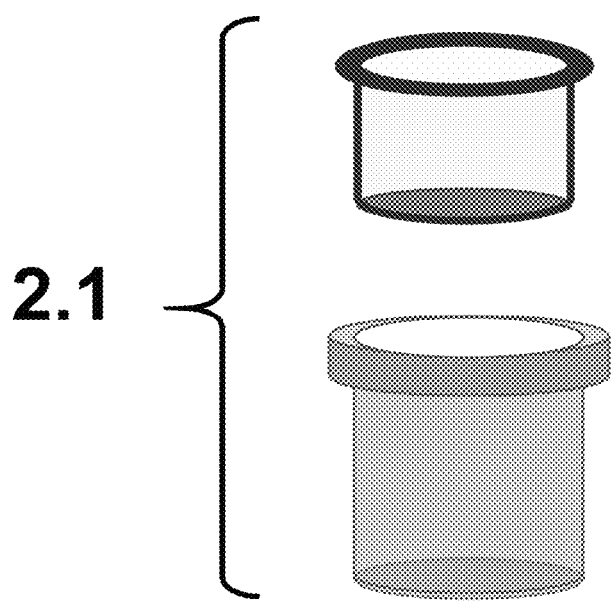
FIG. 2. The ultrafiltration system for double simultaneous filtration in a centrifuge. 2.1—Double membrane cartridge for ultrafiltration in a centrifuge. 2.2—centrifuge tube FIG. 3. Unified module for vacuum ultrafiltration in a centrifuge tube. 3.1—Membrane cartridge for vacuum filtration in a centrifuge tube. 3.2—centrifuge tube. The cartridge and the tube are connected by a vacuum module.
Figure 2:
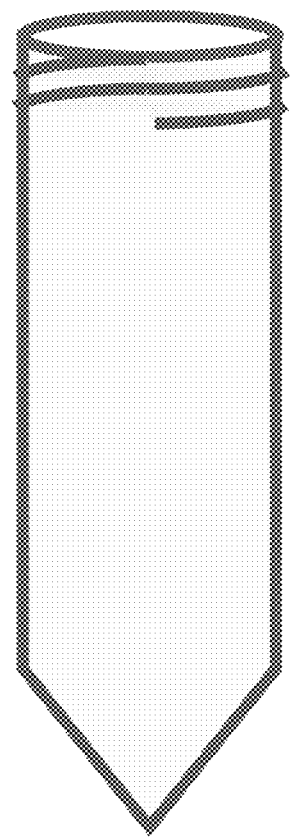

When implementing the method, it is possible to use filter discs, or, in the preferred embodiment, the design of the filtration unit can be a cylinder liner, analogous to the one shown in FIG. 1 and FIG. 2.

Figure 3:
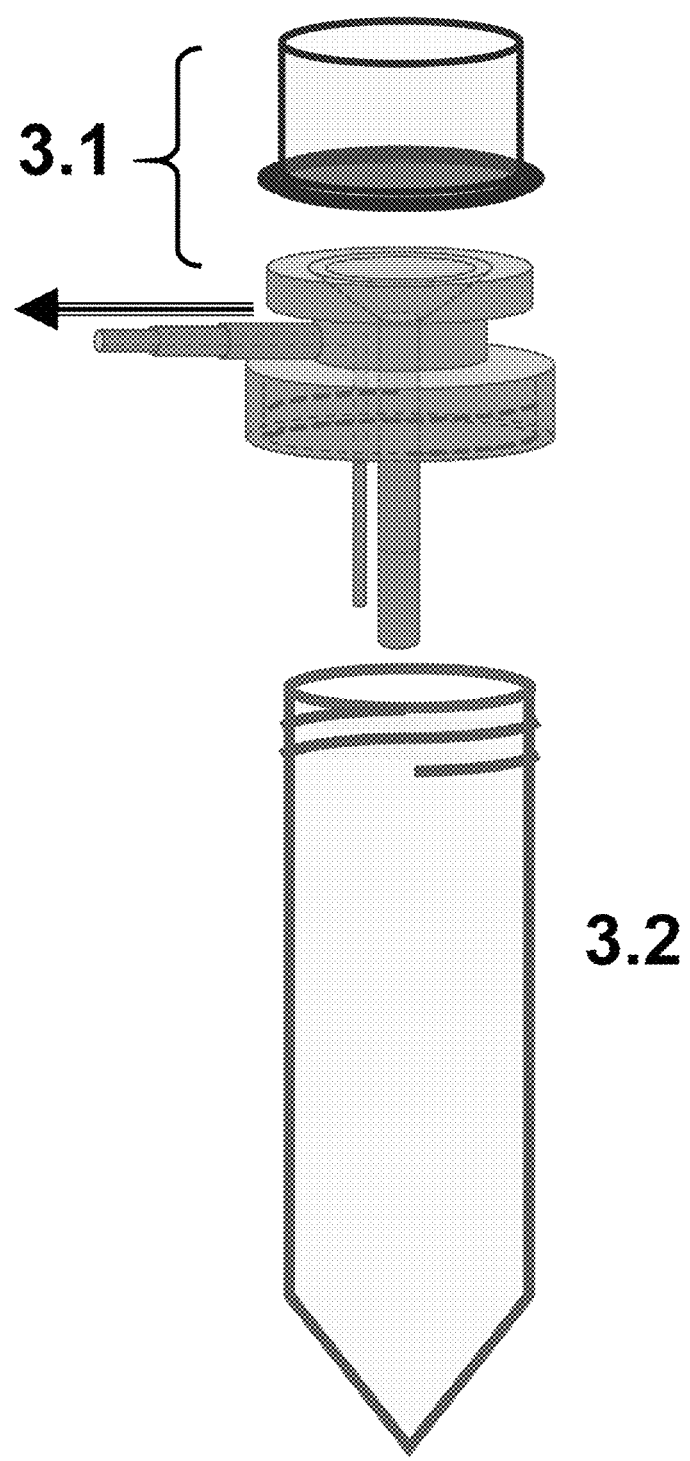
Figure 4:
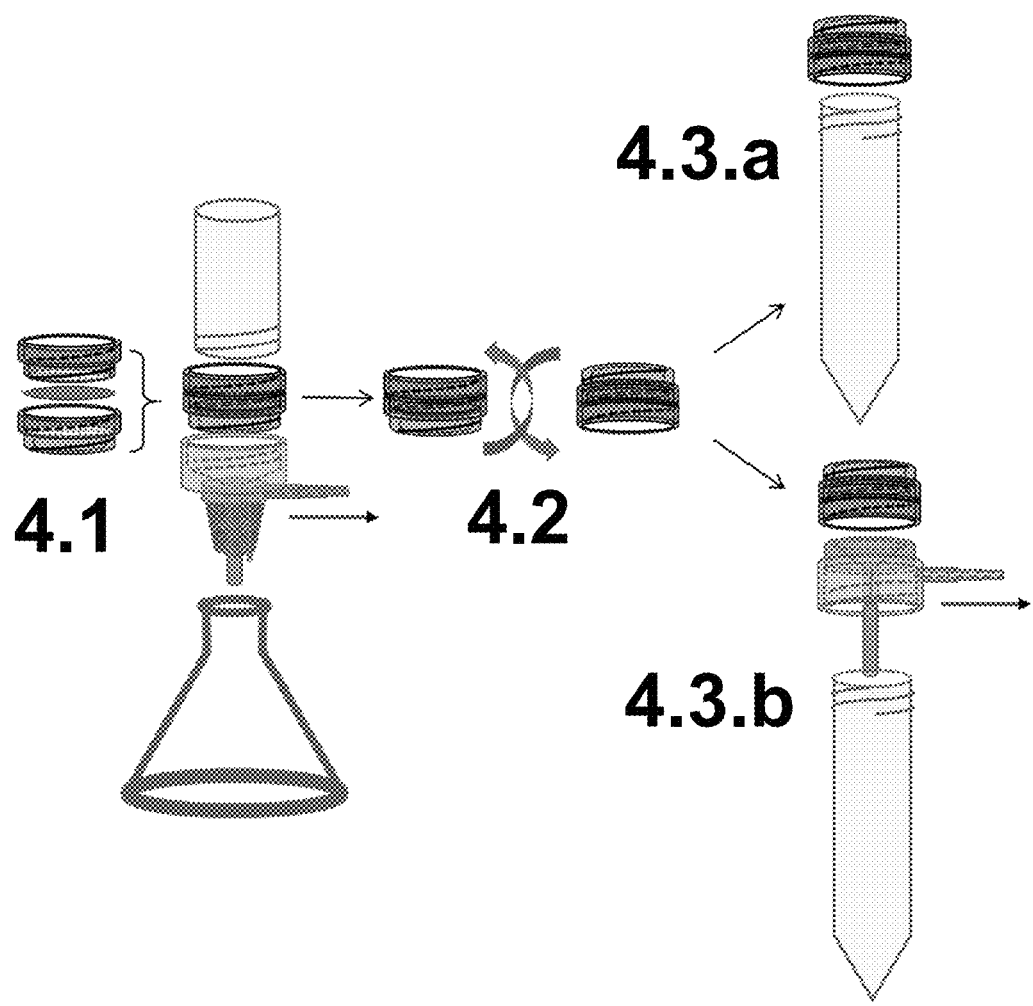
FIG. 4. Unified module for the double side ultrafiltration in the vacuum-centrifuge option (4.3.A) or the vacuum-vacuum option (4.3.B). 4.1—Membrane cartridge for double side ultrafiltration. 4.2.—membrane cartridge backflip.

If required, sequential filtration in vacuum-vacuum, vacuum-centrifuge, centrifuge-vacuum or centrifuge-centrifuge versions can be performed. The unified module for vacuum ultrafiltration into a centrifuge tube is shown in FIG. 3. The unified module for double side ultrafiltration in the vacuum-vacuum or vacuum-centrifuge versions is shown in FIG. 4.

Figure 5A:
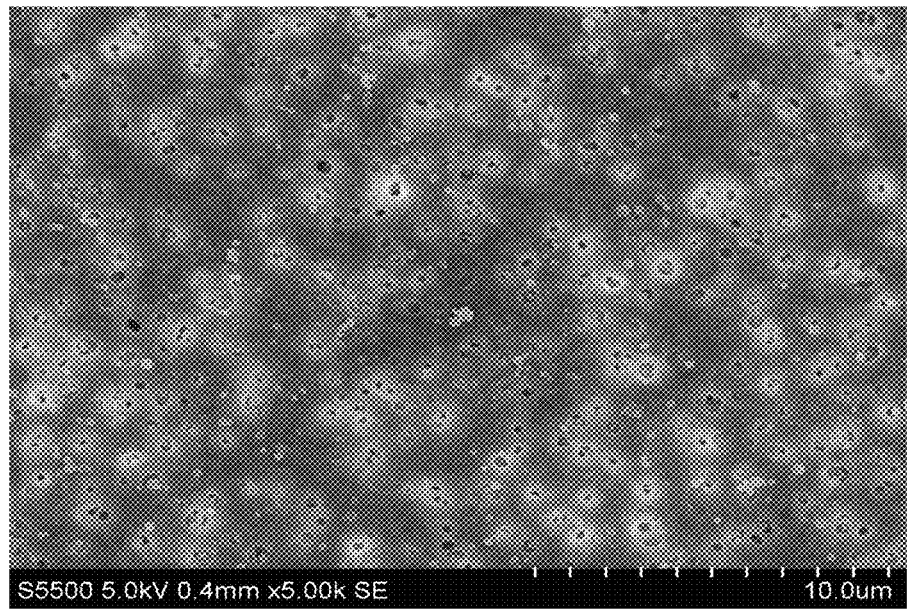
FIG. 5A. Photo of the filter surface with vesicles taken with the use of an electron microscope. The distance between the notches is 1.0 μm.
Figure 5B:
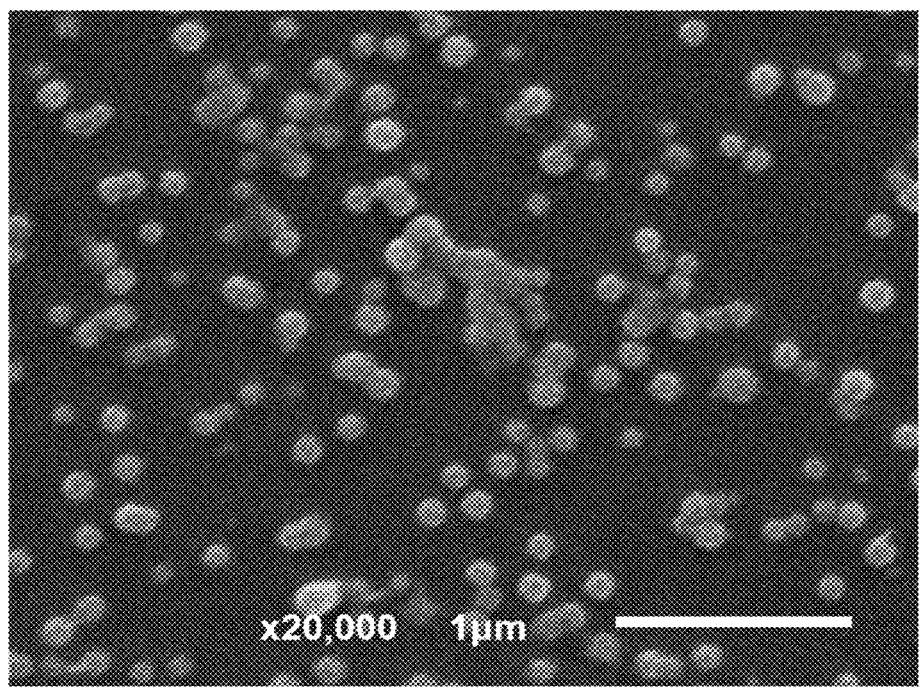
FIG. 5B. Photo of the purified preparation of vesicles taken with the use of an electron microscope. The length of the scale strip is 1.0 μm.

In the preferred embodiments of the invention, the ultrafilters that were used are hydrophilic, lightly charged, not binding to biological polymers, and made from a mixture of cellulose acetates with a porosity of up to 85%. Defects in the structure, as well as functional groups, provide cellulose acetate with insignificant ion exchanging properties that do not result in the binding of biopolymers. An electronic photograph of the filter surface with exosomes on it is shown in FIG. 5A. An electronic photograph of the purified preparation of vesicles (exosomes) is shown in FIG. 5B.

In some embodiments, filtration can be sequential when a sample is passed through the first filter (see FIG. 3), and then through the second filter, otherwise the sample can be passed through two filters at the same time (see FIG. 1 Double vacuum ultrafiltration and FIG. 2. Double ultrafiltration in a centrifuge tube).

In some embodiments, the first, the second, or both stages of filtration are accelerated by vacuum filtration.

In some embodiments, the first, second, or both stages of filtration are accelerated by centrifugation at 3-5,000 rpm.

In some cases, when the initial sample contains a large number of large particles and polymers clogging the first filter, the filtration procedure can be performed after preliminary centrifugation at 10,000 rpm.

In some cases, after preliminary centrifugation at 10,000 rpm, it is possible to obtain a material of such purity that it can be directly filtered through the second filter with pore sizes of 95-200 nm.

In some cases, usually when the researcher is interested in a smaller fraction of exosomes, in order to increase the completeness of their isolation, double side ultrafiltration is performed on the second membrane filter. This method involves filtering by any of the methods described above, after which harvesting of the material obtained is carried out via rinsing with the reverse flow of the rinsing buffer, for example, as shown in FIG. 4, where at the first stage direct filtering through cartridge 4.1 is performed, after that the filter is turned over (4.2) and rinsing is carried out by centrifugation (4.3.$a$) or filtration (4.3.$c$). This is done in order to isolate the smallest exosome fraction, which can penetrate the subsurface layer of the filter, more completely.

It is possible to use a membrane with a substrate or a filter with a modified top layer with the required properties as the second filter.

Examples of the use of the invention in comparison with other methods of purification of exosomes from biological fluids.

For the clinical and diagnostic use of exosomes, it is necessary to have a method for their purification from biological fluids without the use of an ultracentrifuge because clinical laboratories are not equipped with it. Therefore, it is alternatively possible to use (Pin Li, et al., "Progress in Exosome Isolation Techniques", *Theranostics*, 2017, Vol. 7, Issue 3, 789-804) ultrafiltration, concentrating the material using membrane concentrators, and precipitation of exosomes from large volumes of biomaterial by polyethylene glycol. Ultrafiltration can be carried out by passing the biological material through nozzles on syringes (filter syringes) that contain membranes with different pore sizes. The use of concentrators involves centrifugation of the material through membranes at low speed (2,000-4,000 rpm). Exosome precipitation from biological fluids with polyethylene glycol also involves low-speed centrifugation. In this case, it is possible to use conventional centrifuges, which are available in standard clinical laboratories.

The authors have conducted experiments to compare the efficiency of exosome isolation by various published methods in comparison with the claimed method. The experiments were carried out with male urine obtained from anonymous donors. Extracellular vesicles in the urine contain a fraction of prostasomes and can have a size of up to 500 nm.

There was developed a sample collection and storage process. This process allows the accumulation of biomaterial in the quantities required for the test without losing the activity of the studied proteins. The decision was made after a comparative analysis of the samples of the fresh (unfrozen) urine and of the urine after freezing and thawing that was obtained from the same individual. According to the experience, the most convenient protocol for medical practice is to freeze samples at a temperature of −15−−20° C. It is not recommended to store samples at room temperature for more than 3 hours to prevent the reproduction of bacteria present in the urine and to avoid degradation of proteins.

Sterile containers used in standard clinical practice were used to collect urine. It is also possible to use 50 milliliter (ml) centrifuge tubes, such as, for example, a "50 ml centrifuge tube, CELLSTAR®, conical, sterile," or alternative brands. Containers and test tubes must be sterile to ensure repeatability of the analysis procedure. When using non-sterile tubes, there is a risk of bacterial growth that will impact the results of the research.

In the preferred embodiment of the invention, the sample preparation procedure included the following steps: (a.1.) The urine obtained from the patient was centrifuged at a low speed (2,000-3,000 rpm) for 15 minutes; (a.2.) the urine supernatant was placed in 50 ml sterile centrifuge tubes and frozen. After thawing, it was noted that it is necessary to warm the urine sample up to room temperature, constantly stirring (shaking) the tube. The samples that have thawed, but not warmed up contain a major urine protein, uromodulin, in an insoluble form. The use of such samples results in clogging the filters with aggregates of uromodulin and other proteins, which reduces the intensity of the fluid flow through the filter; (a.3.) after defrosting, the samples were incubated for 2-3 hours at room temperature; (a.4.) the urine samples were centrifuged at a speed of 5-10,000 g for 20-30 minutes; (a.5.) 5-20 ml of the supernatant was used for further research.

The quality of exosome isolation was evaluated by the standard Western Blot method using at least two exosome-specific antibodies (CD63 and CD9 antibodies). This allowed to accurately identify the presence of exosomes, and the additional staining of the membrane with Ponceau Red dye allowed to accurately determine the ratio of the target material and the pollutions.

The following exosome isolation methods were tested for comparison: ultracentrifugation; precipitation with polyethylene glycol; a combination of ultracentrifugation and precipitation with polyethylene glycol with various concentrations of polyethylene glycol; sequential filtration of the urine samples using a syringe with filter nozzles with pore sizes of 0.45 µm, 0.22 µm and 0.02 µm; filtering the urine samples through polycarbonate filters with a pore size of 0.01 µm using a vacuum pump; and isolation of exosomes with protein concentrators with membranes of 100,000 and 50,000 Daltons.

When using the ultracentrifugation method, 35 ml of urine was centrifuged at 10,000 g to remove cell debris, then the supernatant was transferred to Beckman centrifuge tubes and the ultracentrifugation was carried out at a speed of 100,000 g for various periods of time. Different time parameters were tested: ultracentrifugation for 3 hours (standard conditions), 5 hours and 12-16 hours. Under standard ultracentrifugation conditions, the yield of exosomes was too small; with an increase of ultracentrifugation time, pollution of the exosomes with urine proteins was observed in some samples, which resulted in occurrence of nonspecific false-positive signals when antibodies were used during Western Blot. As a result, the ultracentrifugation method showed unstable results—the absence or low concentration of exosomes in individual samples or significant contamination of the samples with urine proteins in others.

Polyethylene glycol (PEG) is used in commercial kits for the isolation of exosomes from urine and blood plasma (for example, the ExoQuick-TC kit from Invitrogen, USA). To test the effectiveness of this approach, various amounts of PEG were added to 7 ml of urine to obtain final concentrations of PEG in the urine—5%, 10% and 20%. Then the samples were incubated on ice for 12-16 hours, followed by centrifugation at 10,000 g for one hour. Then, the obtained precipitate was rinsed with physiological saline, lysed, and analyzed by Western Blot method to determine exosomal proteins. It was demonstrated that this method increases the amount of precipitated material compared to the ultracentrifugation method, but, as a rule, these samples also contain urine proteins. These contaminants significantly complicate the analysis of proteins by Western Blot method.

We also used a method of precipitation of exosomes from urine, including pretreatment of the samples with dithiothreitol (DTT) followed by PEG treatment and centrifugation (Kanchi Ravi, R., et al., J. Vis. Exp., 2015, (95), e51158). Although this modification of the PEG precipitation method increased the number of exosomes in the precipitate, the issue of contamination of samples with major urine proteins remained, which led to an increase of the non-specific background in the Western Blot analysis of proteins.

Using a combination of ultracentrifugation and precipitation with polyethylene glycol, 15 ml of urine and various concentrations of PEG (3%, 5%, 10%) were used to reduce the pollution of the exosome samples with urine proteins due to the use of PEG. Then the samples were ultracentrifuged at 25,000 g or 100,000 g for 1 hour. Then, the obtained precipitate was rinsed with physiological saline, lysed, and analyzed by Western Blot to determine exosomal proteins. It was shown that these conditions of isolation do not provide a better result and do not solve the problem of contamination of the samples with urine proteins that co-precipitate with the exosomes.

When exosomes were isolated using a syringe with filter nozzles with pore sizes of 0.45 µm, 0.22 µm and 0.02 µm (filters made by Anatop, USA), 5-7 ml of the sample was used. Then, the exosomes sorbed on a 0.02 µm filter were rinsed with sterile saline and lysed. The lysates were analyzed by Western Blot to determine exosomal proteins. The exosome samples obtained by this method from the urine of patients do not contain urine protein contaminants and are an acceptable material for analysis of the expression of exosomal proteins.

When filtering the urine samples through polycarbonate membrane filters (PCTE) membrane filters with a pore size of 0.01 µm (STERLITECH), 15 ml of urine was used, which had been pre-filtered through filters with pore sizes of 0.45 µm and 0.22 µm. The sample was placed in a funnel containing filters with a pore size of 0.01 µm, and the filtration was carried out by a vacuum pump connected to the funnel. After rinsing the filters with physiological saline, the exosomes retained on the filter with a pore size of 0.01 µm were lysed and analyzed by Western Blot to determine exosomal proteins. It was demonstrated that the samples obtained in this way do not contain significant contamination with urine proteins, but the number of exosomes was significantly lower than that those obtained by filtering urine using a syringe with filter nozzles with pore sizes of 0.45 µm, 0.22 µm, or 0.02 µm.

To isolate exosomes with Sartorius protein concentrators equipped with membranes of 100,000 and 50,000 Daltons, 15 ml of urine was used, that had been preliminary centrifuged at a speed of 10,000 g or filtered through filters with pore sizes of 0.45 µm and 0.22 µm. The concentration of the samples was carried out according to the protocol recommended for this type of concentrators using low-speed centrifugation (3000-4000 rpm). After the centrifugation of the urine, the exosomes sorbed on the membrane of the concentrator were rinsed with two volumes (15 ml each) of physiological saline and lysed in a small (200-400 µl) volume of lysing buffer containing detergents and protease inhibitors. The results of the Western Blot analysis of proteins showed that this method is unacceptable for the isolation of exosomes due to contamination of the samples with major urine proteins (such as uromodulin, immunoglobulins, etc.), which in their native form are larger than 100 kDa and, therefore, are not filtered through concentrator membranes, coprecipitating with the exosomes. In addition, it was almost impossible to ensure the complete elution of exosomes from the membranes of concentrators, despite the use of various lysis buffers containing sufficiently strong detergents (NP-40, SDS) and different temperature conditions of lysis (25° C.-90° C.).

Thus, it can be stated that the method of filtering urine samples using a syringe with a nozzle of 3 filters is the most optimal for isolating exosomes from urine samples in a clinical setting, although it needs to be refined. For example, when using filters, you cannot use more than 5-7 ml of urine to force the sample through a syringe, due to clogging of the pores on the last filter with a pore size of 0.02 μm, which results in extra labor and time consumption.

Another approach for exosome isolation is a salting-out method, which involves the precipitation of exosomes with 0.1 M sodium acetate at pH 4.75 (Brownlee Z, et al., *J Immunol Methods*, May 2014; 407: 120-126). A 1 M solution of sodium acetate, pH 4.75, was added to 15 ml of urine that previously had been centrifuged at a speed of 10,000 g or filtered through filters with pore sizes of 0.45 μm or 0.22 μm to remove the cell debris, to the final concentration of sodium acetate in the solution of 0.1 M Then, the samples were incubated on ice for 30-60 minutes, after that they were heated to 37° C. for 5 minutes and centrifuged at a speed of 5,000 g for 10 minutes (the centrifugation was also tested with increasing time to 30 minutes or 60 minutes). To rinse the exosomes from contamination by urine proteins, the precipitates were resuspended in 0.1 M sodium acetate pH 4.75 solution and the centrifugation procedure was repeated. Then, the precipitated exosomes were resuspended in 200-400 μl of phosphate buffer and analyzed by Western Blot and by analysis of the distribution of nanoparticles on a Zetasizer Nano ZS device (see the results below). The analysis showed that the salting-out method does not provide an amount of exosomes sufficient to carry out an enzyme-linked immunosorbent analysis (ELISA) using multiple protein factors. An increase in the volume of urine samples to 30-50 ml did not solve this problem. The authors' data are consistent with the results obtained in the research (Matias Sáenz-Cuesta, et al., *Frontiers in Immunology*, February 2015, Volume 6, pp. 1-12), where it was shown that the "salting out" method, compared to other methods of exosome isolation methods, provides enough material to study exosomal RNA, but, in comparison with other methods, provides a lower yield of exosome-specific proteins.

Another method described is the isolation of exosomes by binding to particles of silicon carbide (SiC). As described in patent application US 20160333338, "it has been unexpectedly shown that silicon carbide can be used to selectively isolate exosomes from biological fluids." The urine exosome isolation protocol described in US 20160333338 is simple, does not require high speed of centrifugation and, with reproducible results, could be recommended for use in routine clinical practice. The authors have conducted comparative experiments according to the procedure described in US 20160333338. A suspension of silicon carbide powder was prepared by adding 6.25 grams of powder (G/S 2500) to 10 ml of phosphate buffer (pH 7). 15 ml of urine were subjected to low speed centrifugation (1000-3000 rpm) to remove the cell debris. and 400 μl of the suspension of SiC was added to 5 ml of the supernatant. After that, the pH of the mixture was adjusted to pH 8.5 and incubated for 10 min at room temperature. The samples were centrifuged at 2000 rpm, the supernatant was removed and the exosomes were eluted from the silicon particles by incubation in 400 μl of pH 6 phosphate buffer. Analysis of the exosomes by Western Blot and the Zetasizer Nano ZS nanoparticle analyzer, in comparison with other methods used by the authors, showed a relatively small number of exosomes isolated using SiC, as well as contamination of the exosome preparations by soluble urine proteins, and the level of contamination varied from sample to sample. It is interesting to note that a change in the pH of the mixture to 8.5 without the addition of SiC resulted in clouding of the samples, which is possibly related to the precipitation of major urine proteins due to a change in their isoelectric point. Subsequent centrifugation and the precipitation analysis revealed the presence of exosomes in them, which is apparently linked to the mechanical capture of vesicles by the precipitated proteins. Since the method of interaction of exosomes with SiC particles as claimed in US20160333338 does not contain the description of a possible mechanism of the process of selective binding of vesicles to silicon particles, we assume that, under the described conditions, when the urine pH changes, a group of proteins precipitates, and exosomes precipitate as well.

As a result, none of the methods analyzed by the authors led to a result acceptable for implementation in the standard clinical practice. Despite of the availability of commercial kits for isolating exosomes from biological fluids, the search for a cheap and not time-consuming method for standard clinical laboratories continues intensively (Li Pin, et al., *Theranostics*, 2017; 7 (3): 789-804).

For direct comparison of the claimed method of the isolation of exosomes with the most popular competitive methods, as well as for the analysis of the quality and quantity of exosomes isolated from urine samples, the authors used the method of dynamic light scattering (DLS). The Zetasizer NanoZS device (Malvern Instruments, UK) allows to measure dynamic light scattering (DLS) on nanoparticles and, consequently, counting the number of particles in the solution within the size range from 1 nanometer to 3 microns. Analysis of exosome preparations using Zetasizer NanoZS allows to determine the particle size, detect contamination of the sample by co-precipitated urine proteins, and estimate the relative number of exosomes in the sample.

Figure 6:
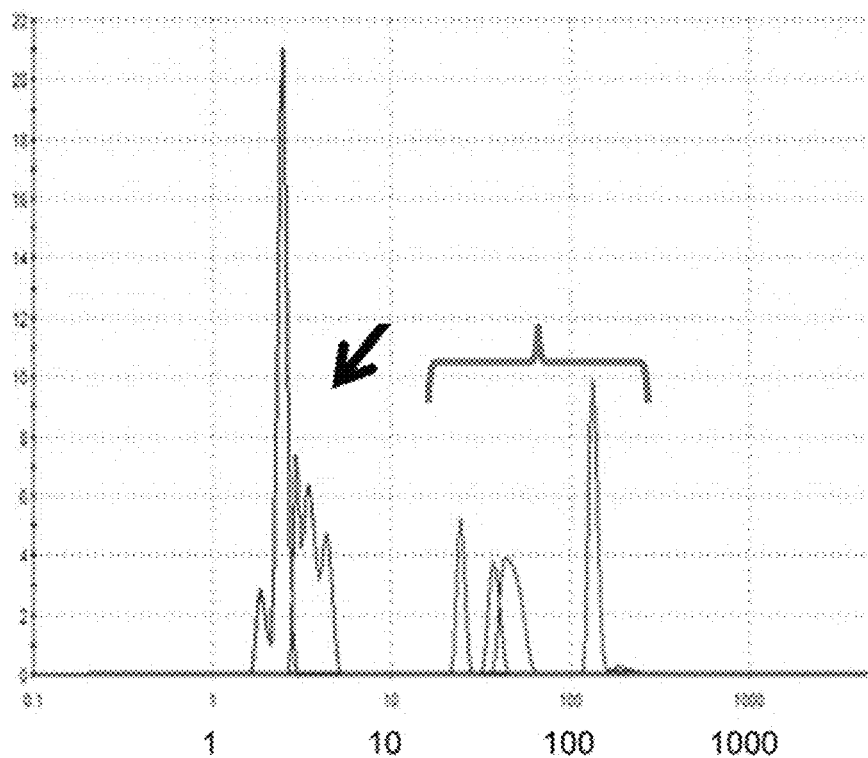
FIG. 6. An example of the of nanoparticles distribution in the sample of exosomes isolated from urine by PEG precipitation, as described in the text below. The test is performed on a Zetasizer NanoZS device at 25° C. The arrow indicates contamination areas with urine proteins, which are observed within the size range from 1 to 10 nm. The exosomes are distributed within the size range of 40-200 nm (the area shown by the bracket). The particle size is indicated on the X axis (in nm).

A typical analysis result of a preparation obtained by exosome precipitation using PEG (which is an analogue of the method used in commercial ExoQuick-TC reagent exosome isolation kits, Invitrogen) is shown in FIG. 6. The analysis by DLS showed significant contamination of the obtained exosome fraction by urine proteins, which results in the appearance of particles from 1 to 10 nm in size. Similar results were achieved for samples obtained using methods with 50 and 100 kDa concentrators (when the exosomes were harvested in the phosphate buffer without lysis) and using ultracentrifugation. The last one method showed less contamination by urine proteins than PEG, but concentration of exosomes was also significantly lower.

Figure 7A:
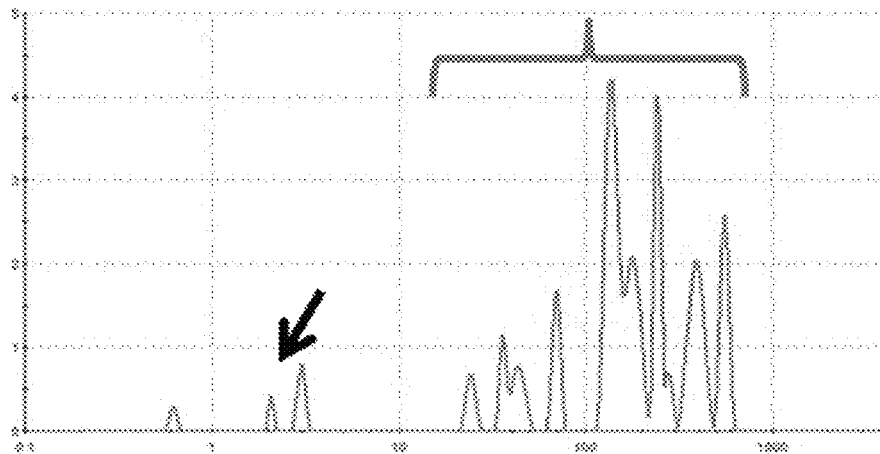
FIG. 7A—the distribution of nanoparticles in the sample according to size (X axis, in nm) and light scattering intensity (Y axis). Urine protein contamination detected by the presence of a signal within 0.8 to 10 nm is indicated by the arrow. The distribution of the exosomes by size is shown by the bracket.
Figure 7B:
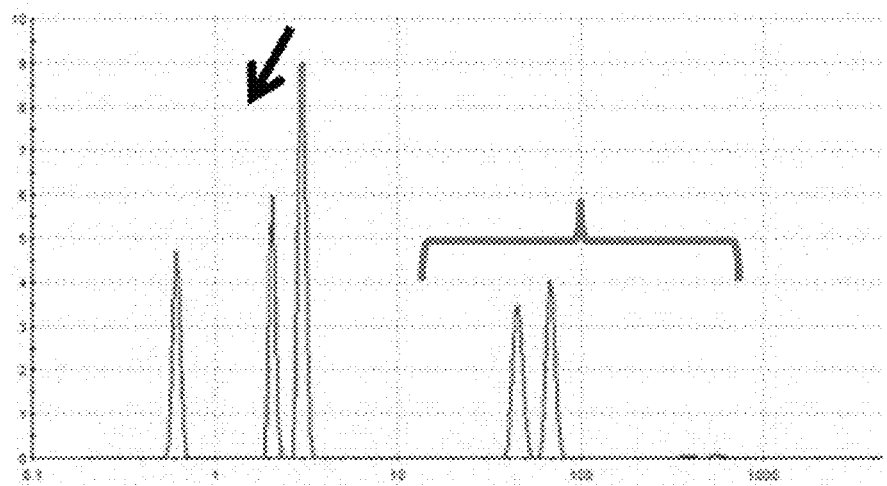
FIG. 7B—Analysis of the same exosome preparation, showing the relative number (Y axis) of particles, defined as protein contamination (in the range 0.8 to 10 nm, X axis) and the relative number of exosomes (the exosome area is shown by the bracket).

The DLS analysis of exosomes isolated by the salting-out method also showed contamination of exosome preparations by urine proteins and the distribution of nanoparticles within sizes of 40-800 nm (FIG. 7). The presence of large (more than 200 nm) particles can be explained by aggregation of exosomes during salting out. As shown in FIG. 7B, the amount of proteins co-precipitated with the exosomes during salting out is significant in relation to the number of pure exosomes.

Figure 8A:
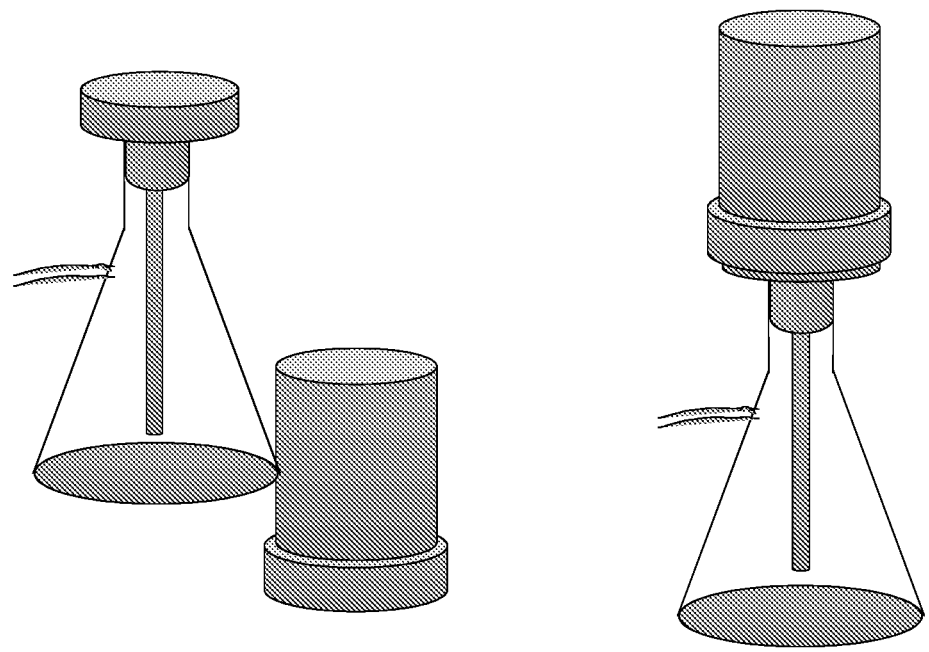
FIG. 8A—a filter for exosomes precipitation is placed on the funnel support. The funnel is placed in a flask to collect the filtered fluid and connected to the vacuum pump.
Figure 8B:
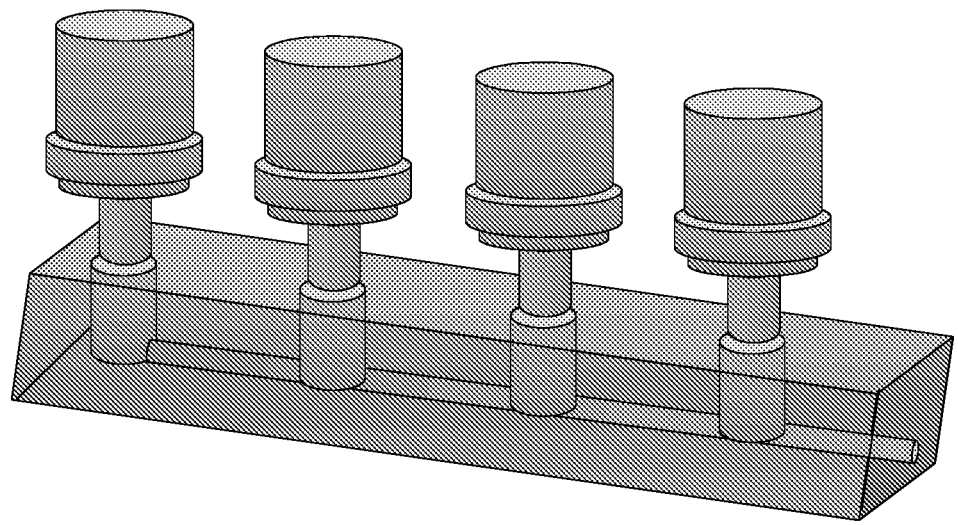
FIG. 8B—The system for the simultaneous isolation of exosomes from four samples.

According to this invention, the process of ultrafiltration of the samples can be carried out on a standard (FIG. 8) vacuum system (can be provided by a vacuum or water-jet pump). After the urine completely passed through the second filter, it was rinsed with 5-15 ml of phosphate-buffered solution as follows: making sure that all the fluid had passed through the filter, but not allowing it to dry, 15 ml of buffer was added to the funnel and passed through the filter. Another rinsing was done. To ensure optimal washing after the last filtration, it is necessary to make sure that all the fluid in the funnel has passed through the filter. After the filtration is completed, the vacuum pump must be turned off and the exosomes located on the filter must be harvested with reversed flow of the buffer. To do that, 400 µl of phosphate buffer is added, followed by pipetting 5-8 times. The exosome suspension can be transferred to an Eppendorf tube and used for a test or stored at −20° C.

Figure 9A:
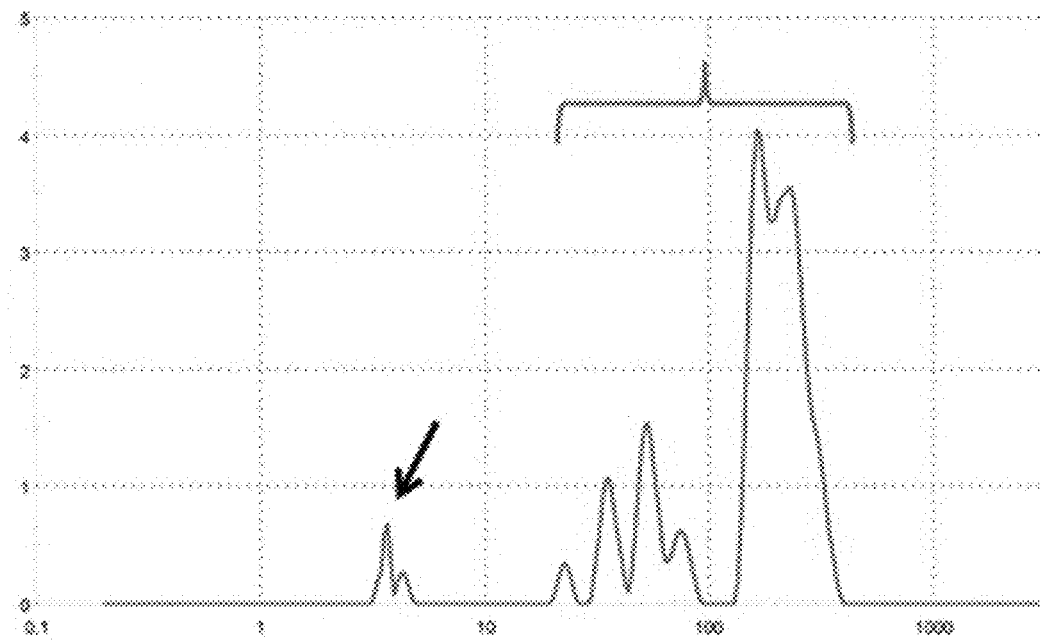
FIG. 9A—the distribution of nanoparticles in the sample according to size in nm (X axis) and light scattering intensity (Y axis). The distribution of exosomes by particle size is indicated by the bracket.
Figure 9B:
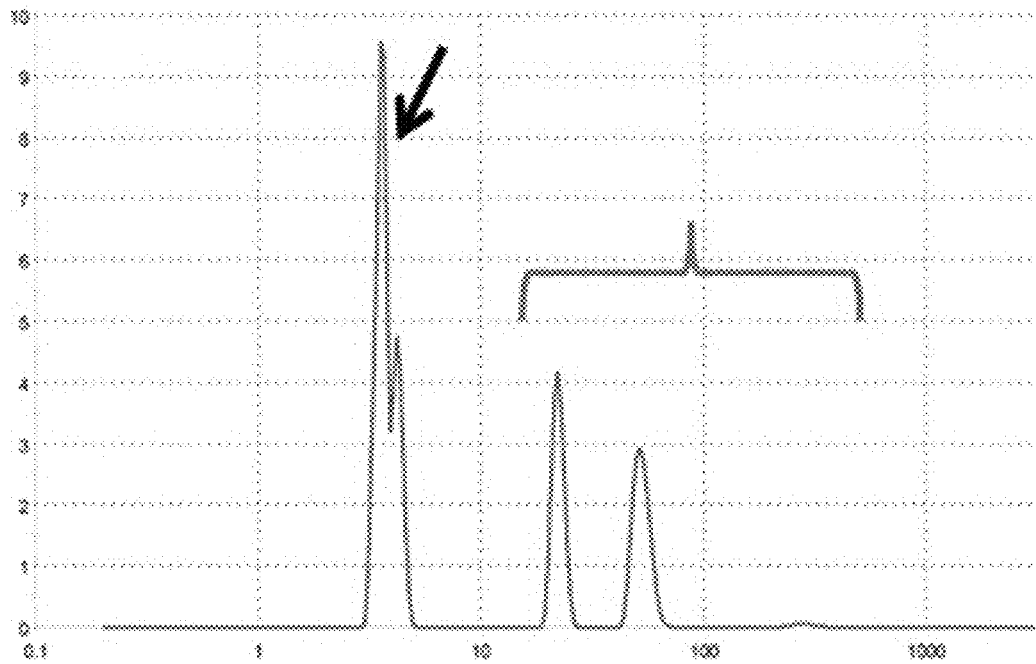
FIG. 9B—Analysis of the same exosome preparation, showing the relative number (Y axis) of particles, defined as protein pollution (ranging from 1 to 10 nm, the X axis) and the relative number of exosomes (the exosome area is shown by the bracket).
Figure 10A:
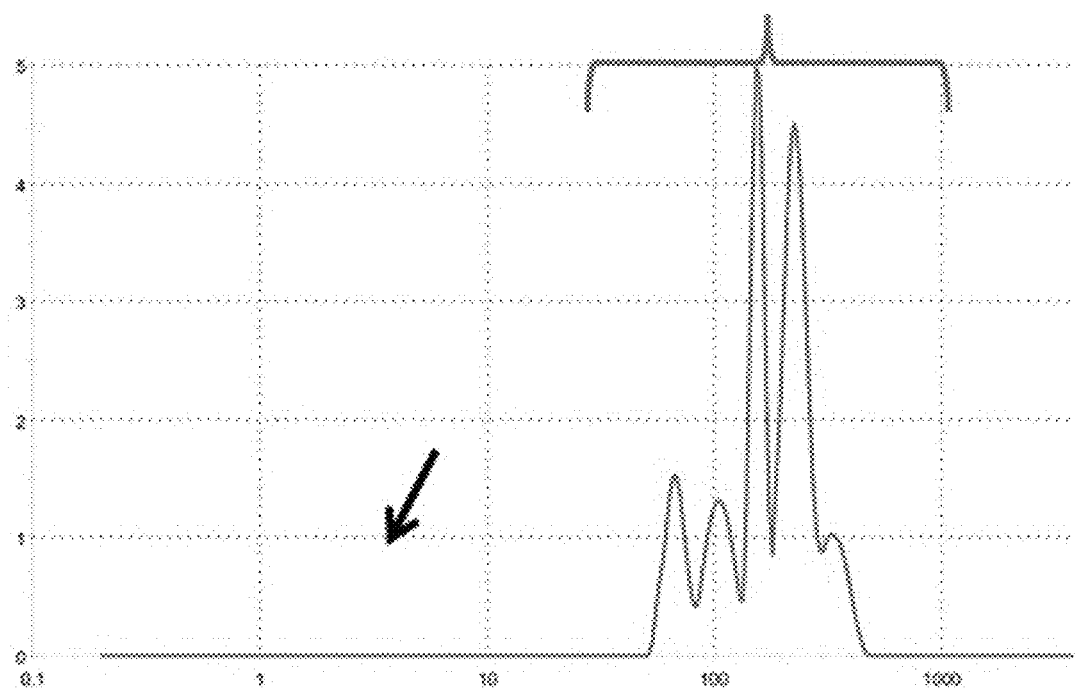
FIG. 10A—the distribution of nanoparticles in the sample according to size in nm (X axis) and light scattering intensity (Y axis). The distribution of exosomes by particle size is indicated by the bracket.
Figure 10B:
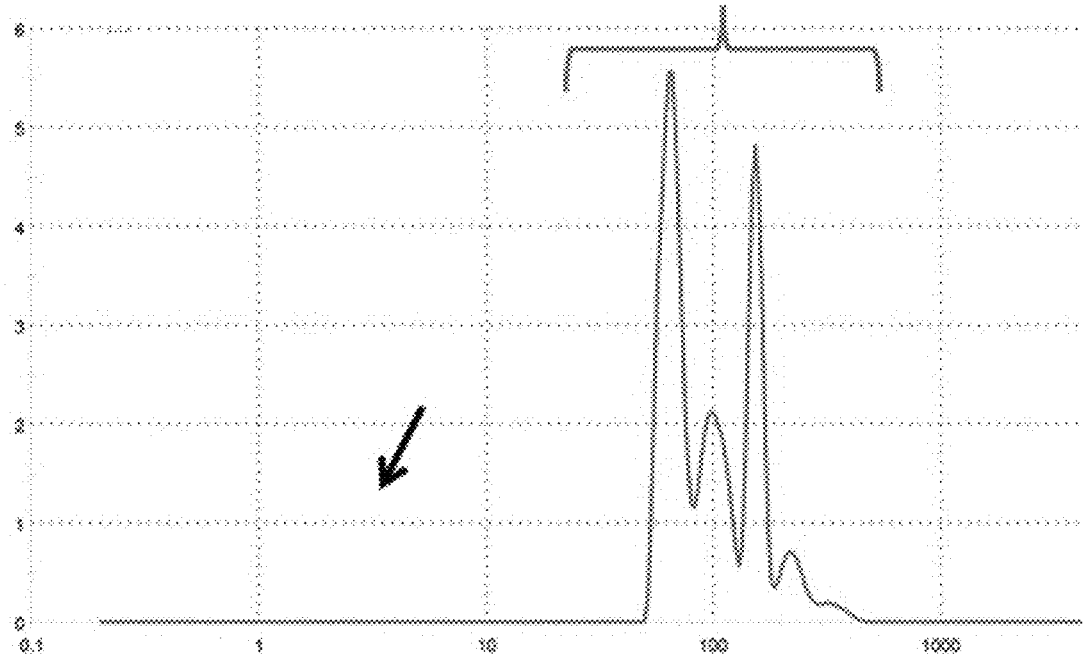
FIG. 10B—Analysis of the same exosome preparation, showing the relative number of particles (Y axis), defined as protein contamination (ranging from 1 to 10 nm, the X axis) and the relative number of exosomes (the exosome area is shown in brackets).

When optimizing the conditions for exosome purification using ultrafiltration the authors used filters based on a mixture of cellulose acetate with different pore sizes: the first filter is 0.45-0.5 µm, the second filter is 0.05 µm, 0.1 µm or 0.15 µm. To evaluate the effectiveness of this method for exosome isolation, the exosome samples obtained by ultrafiltration through membrane filters were analyzed on a Zetasizer NanoZS device. The exosomes isolated on filters with a pore size of 0.05 µm contained urine proteins detected within the range of 1-10 nm (FIG. 9). At the same time, the exosome preparations obtained by filtering urine through 0.1 or 0.15 µm filters were free from contamination and showed the distribution of nanoparticles within the size range, which is common for urine exosomes (FIG. 10). It should be mentioned that the exosome preparations isolated from the clinical urine samples using filters with a pore size of 0.15 µm also did not contain contamination by urine proteins.

In order to evaluate the relative amount of exosomes secreted by the claimed ultrafiltration method, the Zetasizer NanoZS device was calibrated using a known number of nanoparticles with a size of 60 nm. It was shown that the value of 370 kcps (derived count rate) corresponds to $5 \times 10^9$ particles in 1 ml. According to the comparison of the exosome preparations isolated from twenty different urine samples, the method developed, on average, allows to obtain $1.62-2.1 \times 10^9$ exosomes per 1 ml, although there were variations between the samples in the number of exosomes (minimum—$0.48 \times 10^9$ exosomes/ml, maximum—$10 \times 10^9$ exosomes/ml). These values are comparable to the number of exosomes obtained from 15 ml of urine by commercial ExoQuick-TC reagent kits (Invitrogen) and higher than the number of exosomes secreted by Total Exosome Isolation Reagent (Life Technologies) and ultracentrifugation.

Figure 11:
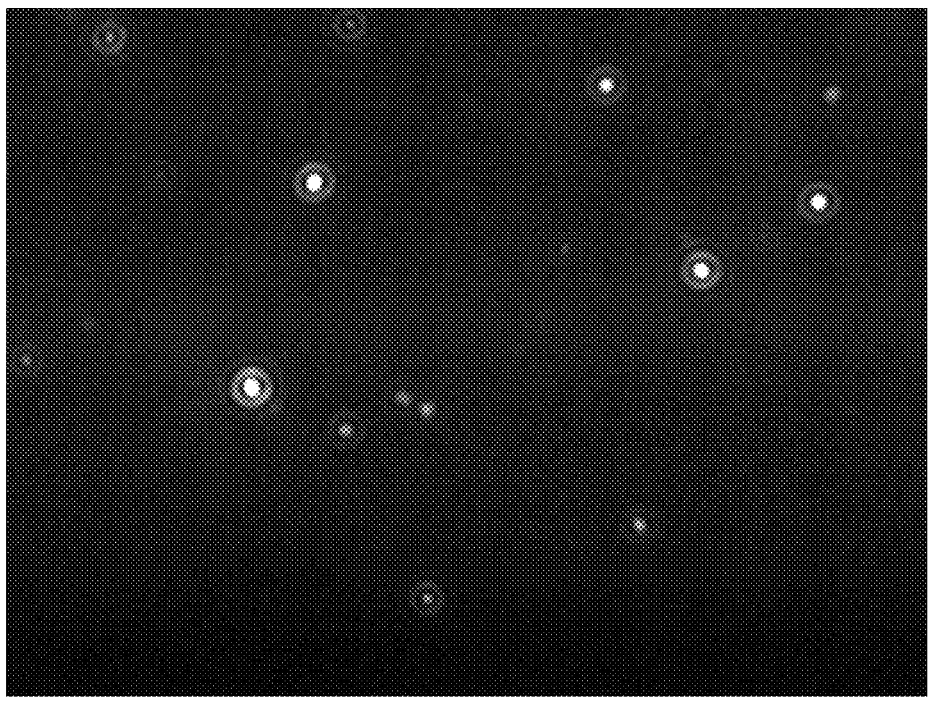
FIG. 11. Photograph of purified exosomes obtained as a still image from a video clip recorded by the NANOSIGHT NS300.
Figure 12:
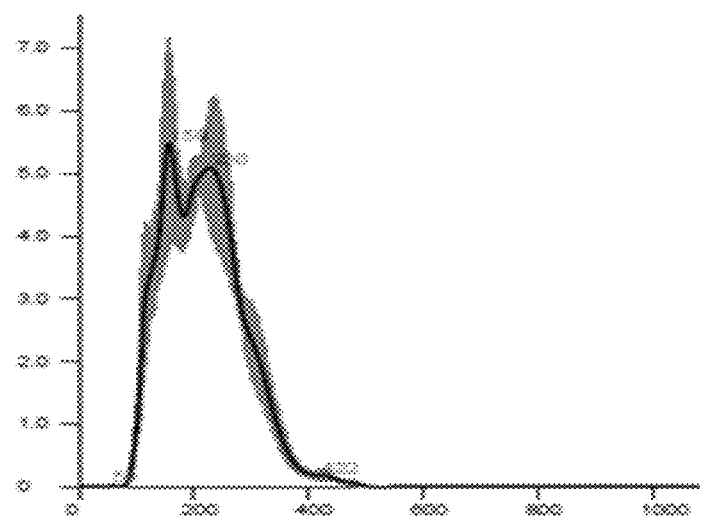
FIG. 12. The curve of the distribution of the extracellular vesicles isolated from urine by size (averaging over 5 samples) obtained on NANOSIGHT NS300.

The final verification of the quality of the isolated extracellular vesicles and their statistical characteristics were obtained on a NANOSIGHT NS300 device (a photograph of extracellular vesicles is shown in FIG. 11, and the average particle distribution of 5 samples is shown in FIG. 12). The peaks in sizes (diameters) of purified extracellular vesicles are observed at approximately 160 nm and 230 nm.

Figure 13:
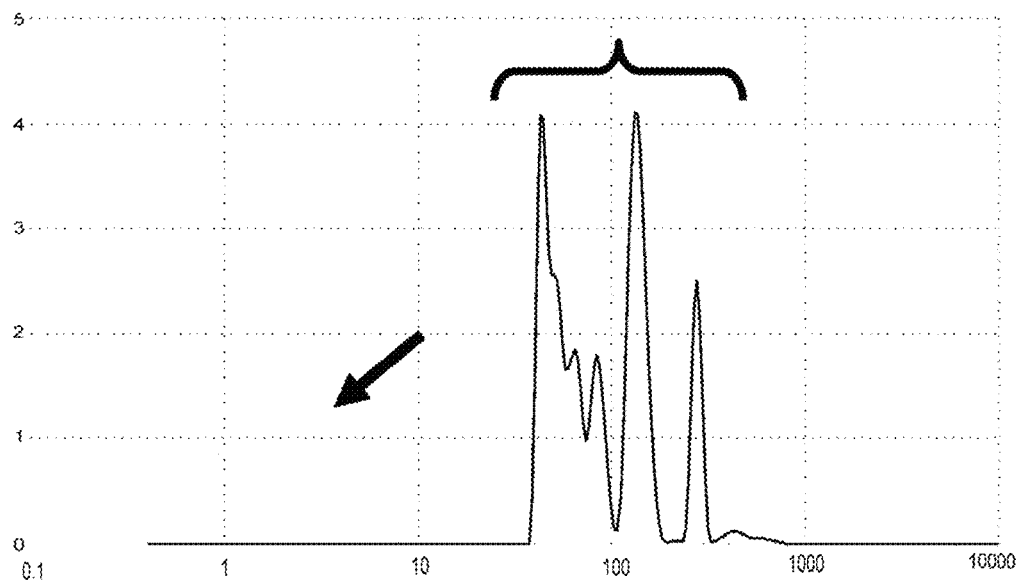
FIG. 13. Analysis of exosomes on a Zetasizer NanoZS device isolated by the claimed method of filtering LnCaP prostate cancer epithelial cells culture fluid using filters with pore sizes of 0.1 μm.
Figure 14:
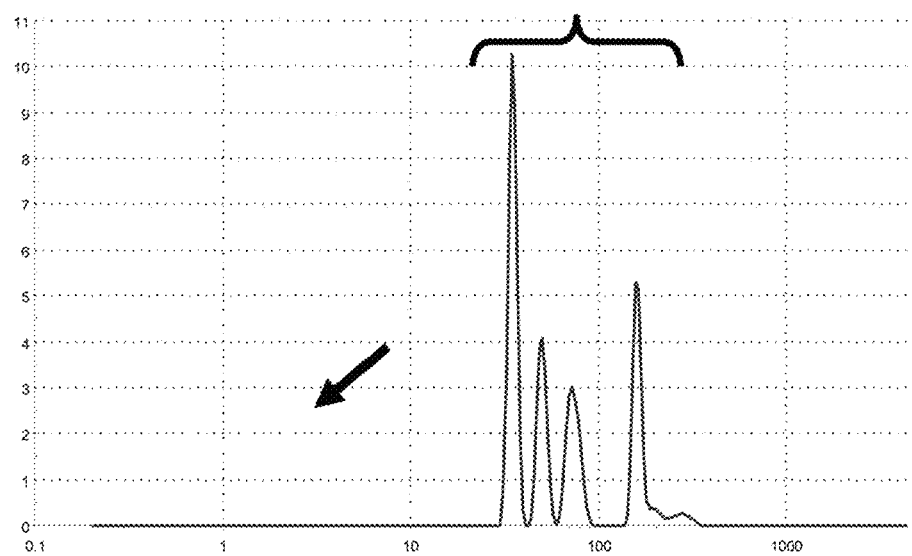
FIG. 14. Analysis of exosomes on a Zetasizer NanoZS device isolated by the claimed method of filtration from human blood plasma using filters with pore sizes of 0.1 μm.

The developed method for the isolation of exosomes was verified using other mammalian biological fluids (for example, blood plasma), as well as a nutrient medium (culture fluid) in which mammalian cells were grown. A curve of the Zetasizer NanoZS analysis of exosomes isolated by the claimed method of filtration from the culture fluid of epithelial cells of prostate cancer LnCaP using filters with pore sizes of 0.1 µm is shown in FIG. 13. FIG. 14 shows a curve of the analysis of exosomes on the device Zetasizer NanoZS, isolated by the claimed method of filtration from human blood plasma using filters with pore sizes of 0.1 µm. Due to the high content of biological material in plasma, in order to apply the claimed method, a 2 ml plasma sample has to be pre-processed, namely, it was diluted 15 times in sterile phosphate buffer to the final volume of 30 ml. Similarly to exosome preparations isolated from clinical urine samples using filters with a pore size of 0.1 µm, the obtained exosome preparations isolated from plasma demonstrated the distribution of nanoparticles within the sizes that are common for exosomes and, did not contain contamination by plasma proteins (FIG. 14).

Thus, the important advantages of this invention are the absence of contamination of the isolated extracellular vesicles or exosomes by proteins, which are present in the processed biological fluid, as well as the simplicity and a low labor consumption of the purification process. The method described allows to effectively purify extracellular vesicles from biological fluids in a standard diagnostic laboratory, that is, without the use of expensive tools, such as an ultracentrifuge. This method can be successfully applied to isolate exosomes from a wide range of animal and human biological fluids, as well as from the conditioned medium of cell cultures. In addition to the application of the claimed purification method for diagnostic purposes (medical indications for the use of this method cover at least the diseases of the organs and tissues of the genitourinary system, as well as cancer), this method is also applicable for therapeutic purposes, when the purified vesicles are used as a delivery agent of a drug to target cells. The reason for this is that during the implementation of this purification method, intact vesicles suitable for further manipulations are formed.

Although the invention has been described with reference to the disclosed embodiments, it should be apparent to specialists in this area that the specific experiments described in detail are only for the purpose of illustrating this invention and should not be construed as in any way limiting the scope of the invention. It should be understood that various modifications are possible without departing from the gist of the present invention.

The invention claimed is:

1. A method for isolating extracellular vesicles from a sample of a biological fluid of a subject, comprising at least the following steps:
    (a) obtaining the sample of the biological fluid;
    (b) passing said sample at least once through a first membrane filter containing a first membrane that practically does not bind biological polymers and has pore sizes in a range from 400 to 600 nm;
    (c) passing a solution that has passed through the first membrane filter from step (b) at least once through a second membrane filter containing a second membrane that practically does not bind biological polymers and has pore sizes in a range from 95 to 200 nm;
    (d) harvesting a material from the sample, which has not passed through the second membrane filter, from a surface of the second membrane filter,
    wherein said material consists essentially of extracellular vesicles.

2. The method according to claim 1, wherein the first or second membrane, which practically does not bind biological polymers, is made of: cellulose acetate, regenerated cellulose, or polyethersulfone.

3. The method according to claim 1, wherein the second membrane filter has pore sizes in a range from 95 to 105 nm.

4. The method according to claim 1, wherein the material that has not passed through the second filter is harvested by a reverse flow of a rinsing buffer.

5. The method according to claim 1, wherein centrifugation or vacuum filtration is used to increase a rate of a biological fluid's passage through the first or second membrane filter.

6. The method according to claim 5, wherein centrifugation or vacuum filtration for purpose of increasing the passage rate is used in any combination, namely, vacuum filtration for the first filter and vacuum filtration for the second filter; vacuum filtration for the first filter and centrifugation for the second filter; centrifugation for the first filter and vacuum filtration for the second filter; centrifugation for the first filter and centrifugation for the second filter.

7. The method according to claim 5, wherein passing the sample of the biological fluid through the first and second membrane filters is carried out at least two times.

8. The method according to claim 1, wherein the biological fluid from which extracellular vesicles are isolated is a human biological fluid, selected from the following group: blood plasma, blood serum, urine, synovial fluid, cerebrospinal fluid, saliva, tear, seminal fluid, milk or prostate juice.

9. The method according to claim 1, wherein medical indications for using the method are selected from diseases of organs and tissues of a genitourinary system, or cancer diseases.

10. A device for implementing the method according to claim 1, the device comprising:
- a first membrane filter containing a first membrane with pore sizes in a range from 400 to 600 nm, and functionally connected to a second membrane filter containing a second membrane with pore sizes in a range from 95 to 200 nm;
- wherein the first and second membranes are made of materials that practically do not bind biological polymers, and the device itself is configured to filter a sample of a biological fluid through both said filters.

* * * * *